(12) United States Patent
Da Silva et al.

(10) Patent No.: US 8,222,605 B2
(45) Date of Patent: Jul. 17, 2012

(54) METHOD FOR DETERMINATION OF THE TOTAL ACID NUMBER AND NAPHTHENIC ACID NUMBER OF PETROLEUM, PETROLEUM CUTS AND PETROLEUM EMULSIONS OF WATER-IN-OIL TYPE BY MID-INFRARED SPECTROSCOPY

(75) Inventors: Monica Teixeira Da Silva, Rio de Janeiro (BR); Geciliane Henriques De Andrade, Rio de Janeiro (BR); Maria Isabel Calicchio Lopes, Rio de Janeiro (BR); Claudia Maria Silva Braga, Rio de Janeiro (BR)

(73) Assignee: Petroleo Brasileiro S.A.—Petrobras, Rio de Janeiro (BR)

( * ) Notice: Subject to any disclaimer, the term of this patent is extended or adjusted under 35 U.S.C. 154(b) by 668 days.

(21) Appl. No.: 12/368,508

(22) Filed: Feb. 10, 2009

(65) Prior Publication Data

US 2009/0294672 A1 Dec. 3, 2009

(30) Foreign Application Priority Data

Jun. 3, 2008 (BR) .................................... 0801639

(51) Int. Cl.
*G01J 5/02* (2006.01)
(52) U.S. Cl. ............................. 250/339.08; 250/339.07
(58) Field of Classification Search ............. 250/339.07, 250/339.08, 343
See application file for complete search history.

(56) References Cited

U.S. PATENT DOCUMENTS

| | | | |
|---|---|---|---|
| 5,420,041 A | 5/1995 | Matsushita et al. | |
| 5,681,749 A | 10/1997 | Ramamoorthy | |
| 5,912,257 A * | 6/1999 | Prasad et al. | 514/356 |
| 7,442,936 B2 * | 10/2008 | Reischman et al. | 250/343 |
| 7,904,251 B2 * | 3/2011 | Martin et al. | 702/22 |
| 2002/0000667 A1 | 1/2002 | Ahn et al. | |

OTHER PUBLICATIONS

D. M. Jones et al., "Determination of Naphthenic Acids in Crude Oils Using Nonaqueous Ion Exchange Solid-Phase Extraction", *Analytical Chemistry*, vol. 73, No. 3, Feb. 2001, pp. 703-707.

John P. Coates, "The Interpretation of Infrared Spectra: Published Reference Sources", *Applied Spectroscopy Reviews*, vol. 31, Nos. 1&2, 1996, pp. 179-192.

Paulo A. da Costa Filho et al., "Aplicação De Algoritmos Genéticos NA Seleção De Variáveis Em Espectroscopia No Infravermelho Médio, Determina Ção Simultânea De Glicose, Maltose E Frutose", *Quim. Nova*, vol. 25, No. 1, 2002, pp. 46-52.

Kenneth R. Beebe, "An Introduction to Multivariate Calibration and Analysis", *Analytical Chemistry*, vol. 59, No. 17, Sep. 1987, pp. 1007A-1017A.

Paul Geladi et al., "Partial Least—Squares Regression: A Tutorial", *Analytica Chemica Acta*, vol. 185, 1986, pp. 1-17.

* cited by examiner

*Primary Examiner* — David Porta
*Assistant Examiner* — Faye Boosalis
(74) *Attorney, Agent, or Firm* — Nixon & Vanderhye P.C.

(57) ABSTRACT

The present invention relates to a method for the determination of the total acid number and naphthenic acid number of petroleum, petroleum cuts and petroleum emulsions of water-in-oil type by mid-infrared spectroscopy utilising correlation between data gathered by means of absorption spectrums obtained with a Fourier-transform infrared spectrophotometer operating in the mid-infrared band equipped with an attenuated total reflectance (ATR) accessory, and acidity results obtained through reference methods utilising a multivariate regression model.

4 Claims, 1 Drawing Sheet

METHOD FOR DETERMINATION OF THE TOTAL ACID NUMBER AND NAPHTHENIC ACID NUMBER OF PETROLEUM, PETROLEUM CUTS AND PETROLEUM EMULSIONS OF WATER-IN-OIL TYPE BY MID-INFRARED SPECTROSCOPY

FIELD OF THE INVENTION

The present invention relates to a method for the determination of the total acid number (TAN) and naphthenic acid number (NAN) of petroleum, petroleum cuts and petroleum emulsions of water-in-oil type utilising the mid-infrared spectroscopy technique, having the objective of permitting application thereof to petroleum emulsions of water-in-oil type containing up to 15% water.

BACKGROUND OF THE INVENTION

The petroleum industry increasingly requires to process petroleum being more corrosive than that traditionally refined, a part of the corrosion occurring during such processing being associated with the presence of naphthenic acids.

Naphthenic corrosion occurs in the temperature band between 180° C. and 370° C., which band is attained in atmospheric and vacuum distillation heating furnaces, in transfer lines from such furnaces to towers, in some distillation tower trays and cut lines, and in some heat exchangers.

The method presently employed to determine petroleum acidity is ASTM D-664, "Standard Test Method for Acid Number of Petroleum Products by Potentiometric Titration", being realised by means of potentiometric titration with potassium hydroxide. The total acid number (TAN) determined in this manner corresponds to the quantity of potassium hydroxide (KOH) required to neutralise each and every type of acid present in 1 g of sample. However the method is not selective for organic acids such as, for example, naphthenic acids, and may even measure acidity arising from the presence of phenols and inorganic compounds having an acid reaction, generating a result which does not correlate with the corrosiveness of the petroleum.

It has been observed that petroleum having a relatively low TAN, in respect whereof promotion of naphthenic corrosion was unexpected, presents such corrosive characteristic in some of the fractions thereof. This occurs by virtue of the fact that this type of corrosiveness does not solely depend on the quantity of naphthenic acids present in petroleum but additionally on the molecular weight of such acids, the types of bonds in the structure thereof, and the boiling points thereof. In addition, in spite of its being widely utilised, the ASTM D-664 method is not the most appropriate for use with petroleum, but is appropriate for use with petroleum derivatives. Such fact prejudices the precision of the said method and m renders the same of limited use in monitoring the processes of removal of naphthenic corrosion from the petroleum currently being studied.

With a view to eliminating such difficulties of correlation of TAN with the corrosiveness of petroleum and its derivatives, a method has been developed for determination of the acidity of petroleum samples arising solely from carboxylic acids present in the sample. The method, published in the journal Analytical Chemistry, v. 73, pp. 703-707, 2001, by JONES, D. M., et al., "*Determination of naphthenic acids in crude oils using non-aqueous ion exchange solid-phase extraction*" discloses a technique wherein organic acids are extracted from the sample by a solid absorbent, being then quantitatively desorbed and eluted, the concentrations thereof being quantified by mid-infrared spectroscopy. Such quantification, on stoichiometric conversion into milligrams of KOH per gram of sample, is denominated naphthenic acid number (NAN). Said publication additionally discloses that the infrared calibration curve is generated through reading solutions of known concentration of a standard commercial range of naphthenic acids through the maximum absorption thereof at approximately 1710 $cm^{-1}$, considering that absorbency of the carbonyl is not influenced by the chemical structure of the acids present.

The objective of infrared (IR) spectroscopy is to identify functional groups in a material by virtue of the fact that each of such groups absorbs at a characteristic infrared radiation frequency. The IR spectrum is created as a consequence of absorption of electromagnetic radiation at frequencies related with the vibration of a given group of chemical bonds in a molecule. The IR spectrum region corresponds to the range in the electromagnetic spectrum lying between visible and radio wave radiation. Said region is divided into three parts: far-infrared (FIR) between 20 and 400 $cm^{-1}$, wherein principally the rotational spectrum of molecules appears; mid-infrared (MIR) between 400 and 4000 $cm^{-1}$, the bands whereof are generated by fundamental transitions and wherein practically all functional groups of organic molecules absorb; and near-infrared (NIR) between 4000 and 12 800 $cm^{-1}$, wherein bands are generated by harmonic transitions and combinations of the fundamental transitions observed in MIR, principally occurring by virtue of the presence of functional groups containing chemical bonds with atoms of hydrogen.

The vibration spectrum of a product is considered as being a unique physical property characteristic of a molecule. Thus an IR spectrum may be used akin to a fingerprint for identification of an unknown pure substance through comparison with a reference spectrum. In the absence of a database including such sample, or in the case of a mixture of products, such analysis assists chemical characterisation through qualitative identification of the functional groups present.

One of the first applications of infrared spectroscopy as an analytical tool occurred during the decade of the 1940s in quality control in German chemical industries (COATES, J. P. "Appl. Spectrosc. Rev.", v. 31, p. 179, 1996). Although infrared spectroscopy furnishes a large quantity of data with respect to the sample the use thereof in the resolution of quantitative analytical chemistry problems became popular only with the technological advances in instrumentation and computing in the 1980s. Instruments capable of generating large quantities of data of high complexity led to the development of chemometry, comprising the application of mathematical and statistical methods for the analysis of chemical and instrumental data (COSTA FILHO, P. A.; POPPI, R. J. "Aplicação de algorítimos genéticos na seleção de variáveis em espectroscopia no infravermelho médio. Determinação simultânea de glicose, maltose e frutose" ["Application of genetic algorithms in the selection of variables in mid-infrared spectroscopy. Simultaneous determination of glucose, maltose and fructose"]—Química Nova, v. 25, pp. 46-52, 2002).

The chemometric methods most utilised for multivariate quantitative analysis are: principal component regression (PCP) and partial least squares regression (PLSR) and analogues thereof.

The principal advantage of utilising multivariate analytical methods is the ability to exactly and precisely predict the value of the desired property of matrices of complex samples subject to chemical or physical interference. This is possible by virtue of the fact that such methods are capable of minimising the influence of interference by means of modelling the spectral variations caused by the interferent, being realised through inclusion of samples possessing the interferents in the multivariate regression model.

Through such methods deriving from principal component analysis (PCA), spectral data (absorption spectrums in the mid-infrared region) is grouped in a matrix X of data, wherein the samples are recorded in the lines, the independent variables (absorbency read at different wave numbers) being in the columns. Consequently the values of the property of interest, also known as dependent variables, are grouped in a matrix Y.

The matrix X is decomposed into various components also known as latent variables or factors constituted by two vectors denominated "loadings" and "scores". The manner whereby such decomposition is realised is the principal difference between the method based on PLSR rather than on PCR.

In PLSR latent variables are found through an interactive process wherein there is an exchange of data between the data of matrix X and of matrix Y. Such process leads to rapid convergence of results and maximises the relationship between dependent and independent variables. This renders the use of PLSR more advantageous than PCR, wherein the decomposition of matrix X is independent of Y.

The mathematical model responsible for predicting the property of interest, also being called multivariate regression model, is constructed from the product of decomposition of matrix X and the data from matrix Y.

The ASTM E-1655 method "Infrared Multivariate Quantitative Analysis" and diverse articles such as, for example, those by GELADI and B. R. KOWALSKI, "Partial Least Squares Regression: A Tutorial", Analytica Chimica Acta, v. 185, 1-17 (1986), K. R. BEEBE and B. R. KOWVALSKI, "An introduction to Multivariate Calibration and Analysis", Analytical Chemistry, v. 59, n° 17, Sep. 1, 1987, pp. 1007A-1017A, and MATENS H. and NAES T., "Multivariate Calibration", John Wiley & Sons, New York, 1989, describe the functioning of the PLSR mathematical algorithm responsible for decomposition of matrices X and Y, resulting in the multivariate regression model.

Construction of a multivariate regression model based on PLSR may be divided into two stages: calibration and validation. Calibration utilises the absorption spectrums of the samples of the calibration population for construction of a mathematical model better adjusted to the spectral data and the values of the desired property. In this stage it is customary to make a selection of the independent variables which shall be utilised in calibration of the muitivariate regression model, the objective whereof is to increase the robustness thereof. Through validation the robustness of the model constructed is verified. This is carried out evaluating the prediction error of the samples of the calibration population (internal validation), also known as cross validation, or of external samples not participating in said calibration (external validation). Normally multivariate regression models are evaluated based on the values of the correlation coefficient ($R^2$) between the values obtained by the proposed alternative technique and the reference values which should be as close as possible to one.

Another parameter employed is prediction error. There exist several ways is of expressing the quality of the model based on the prediction error such as, for example, root mean square error of cross validation (RMSECV) and root mean square error of prediction (RMSEP). Between them, that most utilised is RMSEP.

Equations 1, 2 and 3 show the definitions most used in such evaluation, wherein yi is the value of the property determined by the method of reference, ŷi is the value predicted for sample i of the validation population for the calculation of RMSEP, and N is the number of samples in the population.

$$\text{Residuals(prediction error)} = yi - \hat{y}i \qquad (1)$$

$$\text{Residual variation} = \frac{\sum (yi - \hat{y}i)^2}{N} \qquad (2)$$

$$RMSEP = \sqrt{\frac{\sum (yi - \hat{y}i)^2}{N}} \qquad (3)$$

RMSEP quantifies the magnitude of residuals of the predicted property for the validation samples and is used to determine the precision of predictions for unknown samples. RMSEP should approximate to the error of the method of reference utilised for calibration, and is the error, in the original units, expected in future predictions.

Low RMSECV or RMSEP values may indicate that the model constructed is suitable for predicting the desired parameter of unknown samples, whilst high values suggest that such model is of poor quality.

In the validation stage it is additionally very important to determine the number of latent variables required for construction of the PLSR-based models. For this purpose it is common to utilise the graph of the number of latent variables against the RMSECV value or RMSEP value, depending on the type of validation utilised.

A very low number of factors may result in high prediction errors by virtue of exclusion of variables having important information with reference to the property of interest. Thus excessive use of factors in addition to increasing complexity of the model, may lead to an increase in prediction error due to the excessive adjustment of the model wherein noise has been included.

RELATED ART

United States patent US 2002/000667 of Exxon Mobil Research and Engineering Company discloses a method for determination of the total acid number (TAN) by Fourier transform infrared spectroscopy utilising a heated transmission cell and chemometric treatment of the data. However, the complexity of mounting such transmission cell together with the difficulties in operation thereof greatly increase analytical time to the point of permitting the execution of a maximum of two samples per day. In addition thereto, as in the development of the multivariate regression model, it is necessary to establish an operating temperature, diverse models would require to be generated by virtue of the fact that it is not possible to work with samples having greatly differing physico-chemical properties at a single temperature.

U.S. Pat. No. 5,420,041 and U.S. Pat. No. 5,681,749 also disclose methods having general characteristics similar to that cited in the above patent, however none thereof render possible the simultaneous determination of TAN and NAN of petroleum, petroleum cuts and petroleum emulsions of water-in-oil type nor are they shown to be specific for detection of organic acids, as is the method of the present invention.

The aspect distinguishing the method of the present invention from other methods comprising the present state of the art is employment of the technique of attenuated total reflectance (ATR), conferring on the method greater practicality and rapidity in obtainment of data, rendering possible the implementation thereof in industrial plants for process control, principally with respect to removal of naphthenic acidity with greater reliability.

The technique of attenuated total reflectance is based on the phenomenon of total reflection of radiation falling on the interface between materials having different refractive indices. Such technique is utilised to avoid interferents in the fingerprint of the spectrum of thin films. It is of great utility for examining dense materials or those having high absorption whereby transmission is not possible.

Such type of problem is commonly encountered in situations wherein the solvent such as, for example, water behaves as interferent through presenting characteristic stretchings in the same region of absorption as the species of interest, rendering analysis by traditional methods unviable.

The present invention has as the object thereof a method based on the foregoing technique which same presents additional advantages among which may be cited:
(i) readings on crude samples dispensing with prior treatment, the sample being enabled to contain salt and up to 15% water;
(ii) utilisation of the same mathematical model independently of the type of sample and of the physico-chemical properties thereof;
(iii) repeatability exceeding that of the reference methods;
(iv) non-utilisation of solvent;
(v) reduction in waste disposal.

These and other advantages shall be obvious to specialists in the field from the detailed description of the invention.

SUMMARY OF THE INVENTION

The present invention relates to a method for the determination of total acid number and naphthenic acid number of petroleum, petroleum cuts and petroleum emulsions of water-in-oil type through mid-infrared spectroscopy, comprising the following stages:
a) Submission of samples of petroleum, petroleum cuts and petroleum emulsions of water-in-oil type for analysis by infrared radiation at ambient temperature in a Fourier transform infrared spectrophotometer operating in the mid-infrared band possessing an attenuated total reflectance accessory, obtaining the respective infrared spectrums;
b) Determination of total acidity of such samples through correlation between values obtained by potentiometric titration with potassium hydroxide and values obtained through the absorption spectrums obtained in the foregoing stage a) utilising a multivariate regression model;
c) Determination of naphthenic acidity of such samples through correlation between values obtained through solid-phase extraction and values obtained through the absorption spectrums obtained in the foregoing stage a) utilising a multivariate regression model.

BRIEF DESCRIPTION OF THE FIGURES

The method for the determination of the total acid number (TAN) and naphthenic acid number (NAN) of petroleum, petroleum cuts and petroleum emulsions of water-in-oil type by mid-range infrared spectroscopy, object of the present invention, shall now be described in detail based on the figures referred to below forming an integral pad of the present specification.

DETAILED DESCRIPTION OF THE INVENTION

Figure 1:
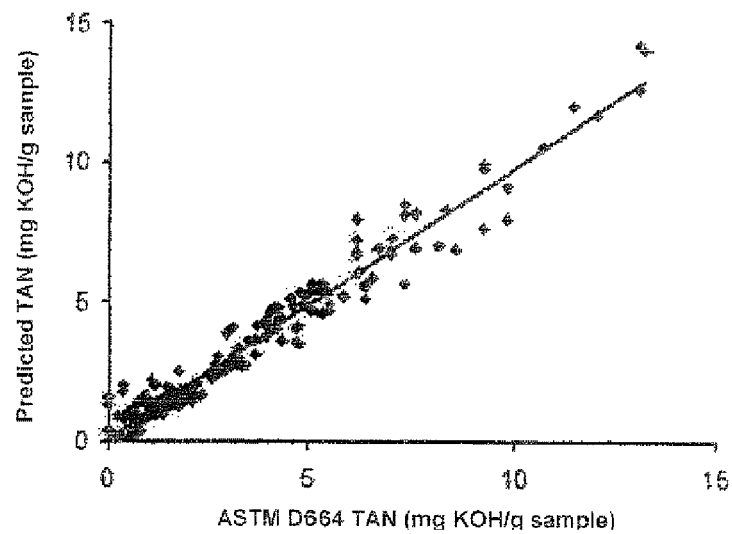
FIG. 1 shows values predicted by the multivariate regression model and those measured by the ASTM D-664 method for TAN, utilising samples of petroleum and petroleum cuts having an acidity between 0.05 and 15 mg KOH per g of sample.

With the objective of the method for the determination of the total acid number (TAN) and naphthenic acid number (NAN) of petroleum, petroleum cuts and petroleum emulsions of water-in-oil type by mid-infrared spectroscopy being better understood and evaluated it shall now be described in detail by means of the following stages.
Sample Selection For carrying out the method of the present invention 206 samples were analysed deemed to be representative of national petroleum and the respective cuts thereof, being the samples destined for determinations of TAN and NAN. The TAN and NAN bands of said samples were planned to range between 0.05 and 15.0 mg KOH per g, in addition to ensuring that the same should possess sufficiently different physico-chemical properties, that is to say the calibration samples were selected such as to cover the maximum possible variability to be found in the validation samples, consequently rendering possible an accuracy appropriate for the determinations it is intended to make.
Obtainment of Infrared Spectrums Fourier transform infrared (FTIR) spectrums of said samples were obtained at ambient temperature in the band from 21° C. to 28° C. in a Thermo Nicolet infrared spectrophotometer, NEXUS 670 model, in the mid-infrared (MIR) spectral range from 650 $cm^{-1}$ to 4000 $cm^{-1}$, utilising an attenuated total reflectance accessory equipped with a zinc selenide (ZnSe) crystal having approximately 12 reflections.
Determination of Total Acidity and Naphthenic Acidity In a first stage the total acid numbers (TAN) of the samples analysed were determined through potentiometric titration with potassium hydroxide as established by The ASTM D-664 method "*Standard Test Method for Acid Number of Petroleum Products by Potentiometric Titration*". For the determination of the naphthenic acid number (NAN) the solid-phase extraction method developed by JONES, referred to previously, was utilised.

The multivariate regression models were carried out employing the program "*Unscrambler 9.2*" produced by Camo Technologies.

The spectral ranges selected for carrying out the calibration were obtained from the preliminary analysis of the regression coefficients for a PLSR calibration containing the 206 calibration samples having TAN's and NANs between 0.05 and 15 mg KOH/g, the entire range from 650 $cm^{-1}$ to 4000 $cm^{-1}$ being used.

Based on said initial analysis with assistance from the graph of regression coefficient against independent variables, selection was made of the spectral bands permitting minimisation of prediction error. The wave number bands relevant for construction of the TAN and NAN multivariate regression models were: 1002-1351 $cm^{-1}$ and 1550-1822 $cm^{-1}$.

The data was centred around the mean and complete cross validation was utilised for optimisation. In centring the data around the mean the values of each variable were subtracted from the mean value of the variable, eliminating the requirement for a constant term in the models.

By virtue of the fact that in these experiments products were utilised having differing physico-chemical natures, that is to say the population of samples was wide-ranging including a large number of samples of petroleum, petroleum cuts and petroleum emulsions of water-in-oil type from various sources, inconsistent results were not encountered and no sample was withdrawn from the calibration data population.

The results of external validation of the regression models for predicting TAN and NAN are shown in Tables 1A and 1B, respectively.

TABLE 1A

| Sample | TAN (mg KOH/g) | |
|---|---|---|
| | ASTM D664 (1) | FTIR-MIR |
| Petroleum A | 0.78 (I); 0.70 (OB); 0.61 (IB) | 1.02 |
| Petroleum B | 1.41 (I); 1.30 (OB); 1.13 (IB) | 1.34 |
| Petroleum C | 1.17 (I); 1.07 (OB); 0.97 (IB) | 1.35 |
| Petroleum D | 0.63 (OB) | 0.42 |
| Petroleum E | 9.80 (I); 8.25 (OB); 6.67 (OB) | 9.44 |
| Cut A | 2.84 (OB) | 2.83 |
| Cut B | 3.15 (I); 2.95 (OB); 2.54 (IB) | 2.96 |
| Cut C | 4.76 (I); 4.53 (OB); 4.29 (IB) | 4.71 |
| Cut D | 13.20 (OB) | 13.85 |
| Cut E | 4.73 (OB) | 4.15 |
| Cut F | 5.77 | 5.29 |

(1) Standard ASTM D664 utilising the inflection point (I) or organic buffer (OB) or inorganic buffer (IB)

TABLE 1B

| Sample | NAN (mg KOH/g) JONES (2) | NAN (mg KOH/g) FTIR-MIR |
|---|---|---|
| Petroleum F | 0.59 | 0.73 |
| Petroleum G | 0.87 | 1.03 |
| Petroleum H | 0.86 | 1.01 |
| Petroleum I | 0.23 | 0.35 |
| Petroleum J | 7.76 | 7.62 |
| Cut G | 2.21 | 2.34 |
| Cut H | 2.50 | 2.33 |
| Cut I | 3.56 | 3.81 |
| Cut J | 13.60 | 12.20 |
| Cut L | 3.04 | 3.37 |
| Cut M | 4.35 | 4.43 |

(2) Method of JONES, D. M. et al., published in the journal Analytical Chemistry, v. 73, pp. 703-707, 2001.

The number of latent variables (LV=2 in both models) for construction of the multivariate regression model was defined through analysis of the graph of RMSEP against LV number. The models selected represent at least 95% of the total variance of X and 96% of the variance of Y.

Figure 2:
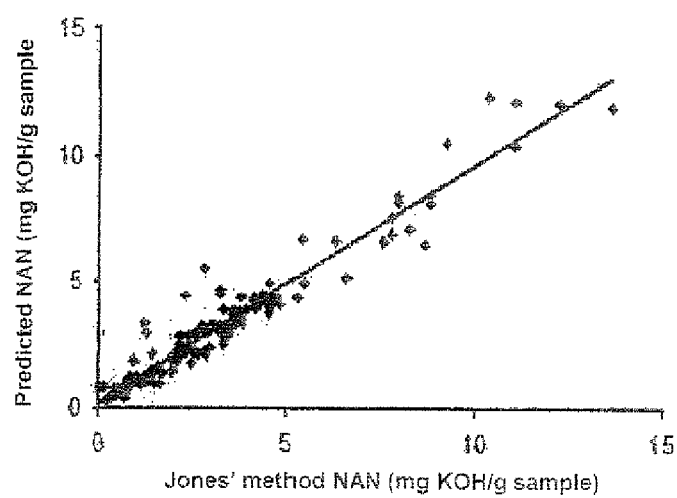
FIG. 2 shows values predicted by the regression model and those measured by the method developed by JONES for NAN, utilising samples of petroleum and petroleum cuts having an acidity between 0.05 and 15 mg KOH per g of sample.

The values predicted for acidity, both total (TAN) and naphthenic (NAN), through FTIR-MIR were very close to the values determined by the standard method and by the JONES method, as shown in FIG. 1 for TAN values, wherein $R^2=0.9760$, and FIG. 2 for NAN values, wherein $R^2=0.9678$.

For determination of naphthenic acid number (NAN) as recommended by the JONES method cited above, organic acids were extracted from the sample by means of a solid absorbent and quantified by mid-infrared spectroscopy.

Obtainment of Calibration Curves

The infrared calibration curve for TAN determination was carried out by the PSLR method, correlating each measurement of TAN with the ASTM D-664 standard method at the absorbencies measured in the infrared spectrum.

The infrared calibration curve for NAN determination was realised through reading solutions of known concentration of a standard commercial range of naphthenic acids by means of the maximum absorption at approximately 1710 cm$^{-1}$, it being considered that carbonyl absorbency is not influenced by the chemical structure of the acids present. The sample was absorbed in a packed cartridge the solid phase whereof being preferentially constituted by a weak ion exchanger of the gamma-aminosilica type, followed by desorption carried out with mixtures of acetone and methanol. Optionally a strong ion exchanger may be utilised based on a silica support and acrylamide copolymer modified by trimethylalkylammonium chloride groups, followed by desorption with a 2% mixture by volume of formic acid in methyl tert-butyl ether.

The methodology of NAN determination by direct reading in the infrared of the present invention without the extraction stage has been shown to be more efficient than the JONES method for light petroleum cuts, wherein the extraction stage frequently leads to complete loss of carboxylic acids, erroneously indicating the absence of corrosiveness in the sample.

In addition it has been possible to show that, in samples the results whereof gave significant deviation values in relation to the results obtained with the reference methods and high residuals in the results predicted by infrared, there was an error in the analyses carried out by the reference methods. This fact was confirmed on repetition of TAN determinations by the standard ASTM D-664 method on the said samples with discrepant results, leading to results approximating those obtained by FTIR and very different from the values initially used as reference. Analyses of petroleum samples L and M shown in Table 2, carried out prior to and following making predictions of TAN by infrared, demonstrate this fact.

TABLE 2

| Sample | TAN (mg KOH/g) ASTM D664 (1) | TAN (mg KOH/g) FTIR-MIR |
|---|---|---|
| Petroleum L (prior to FTIR prediction) | 3.47 (OB) | 1.46 |
| Petroleum L (subsequent to FTIR prediction) | 1.65 (I)-1.44 (OB) −1.20 (IB) | 1.64 |
| Petroleum M (prior to FTIR prediction) | <0.05 (OB) | 1.36 |
| Petroleum M subsequent to FTIR prediction) | 1.40 (I)-1.10 (OB) | 1.57 |

(1) Standard ASTM D664 utilising inflection point (I) or organic buffer (OB) or inorganic buffer (IB)

Analysis of precision of the method was carried out utilising three representative samples of the regression model. Spectrums were obtained from samples N, O and P having differing aliquots, and repeatability was calculated following the procedure recommended by the ASTM E-177 method "*Standard Practice for Use of the Terms Precision and Bias in ASTM Test Methods*" (applying equation 4).

$$r = t_{95\%} \cdot 2^{1/2} \cdot S \qquad (4)$$

Where: S is the standard deviation of the values obtained for replicates of the samples and $t_{95\%}$ is the Student's constant for 95% of the range of confidence.

Table 3 shows values of the mean, of the standard deviation, of the level of confidence and of the repeatability of infrared analyses. Also shown are values of standard deviation of different TAN measurements by the ASTM D-664 method carried out in a single laboratory. This study suggests good repeatability of TAN measurements by infrared in comparison with measurements determined by the ASTM D-664 method,

TABLE 3

| | ASTM D-664 (1) | | | | FTIR-MIR | | | | |
|---|---|---|---|---|---|---|---|---|---|
| Sample | TAN (mg KOH/g) | Standard deviation | Mean | Level of confid. (95%) | TAN (mg KOH/g) | Standard deviation | Mean | Level of confid. (95%) | Repeatability (r) |
| N | | 0.332 | 1.52 | 0.41 | 1.47 | 0.035 | 1.52 | 0.03 | 0.12 |
| | 2.10 | | | | 1.56 | | | | |
| | 1.44 | | | | 1.57 | | | | |
| | 1.41 | | | | 1.53 | | | | |
| | 1.41 | | | | 1.51 | | | | |
| | 1.25 | | | | 1.51 | | | | |
| | | | | | 1.48 | | | | |
| O | 10.28 | 0.721 | 9.54 | 0.67 | 9.10 | 0.094 | 9.04 | 0.09 | 0.32 |
| | 10.33 | | | | 9.13 | | | | |
| | 9.16 | | | | 8.98 | | | | |
| | 9.34 | | | | 9.09 | | | | |
| | 8.26 | | | | 8.86 | | | | |
| | 9.89 | | | | 9.08 | | | | |
| | 9.51 | | | | 9.04 | | | | |
| P | 4.38 | 0.377 | 4.20 | 0.35 | 5.52 | 0.036 | 5.49 | 0.03 | 0.12 |
| | 4.73 | | | | 5.55 | | | | |
| | 4.38 | | | | 5.47 | | | | |
| | 4.18 | | | | 5.47 | | | | |
| | 4.19 | | | | 5.50 | | | | |
| | 3.52 | | | | 5.44 | | | | |
| | 3.99 | | | | 5.51 | | | | |

(1) ASTM D664, utilising organic buffer (OB) as reference

Applicability of the Method to Emulsions

With the objective of assessing the applicability of the method of TAN determination by FTIR for emulsions, petroleum samples containing up to 15% of water by weight were evaluated. The multivariate regression model carried out on samples of petroleum and petroleum cuts furnishes good results, even in the absence of emulsions in the training samples matrix, as examples in Table 4 show.

As water content increases an increase in the number of latent variables in the said model improves predictive capability of the value of TAN. This is the case for samples having a water content exceeding 5%. It is known that the presence of water influences TAN determination by the ASTM D-664 method. In some samples evaluated containing between 15% and 50% water the predicted values of TAN by FTIR were better than those determined by the reference method and coherent with those obtained following dehydration of the sample.

TABLE 4

| Sample | Water content, % (1) | TAN ASTM D664 (2) (mg KOH/g) | Temp. (° C.) | Predicted TAN LV = 2 (3) | | Predicted TAN LV = 3 (3) | |
|---|---|---|---|---|---|---|---|
| | | | | Predicted | Deviation | Predicted | Deviation |
| Q | 0.15 | 3.55; 3.27 | 22 | 3.28 | 1.23 | 2.75 | 0.54 |
| R | 1.13 | 3.00; 3.20 | 22 | 3.17 | 0.62 | 2.89 | 0.29 |
| S | 6.00 | 2.94; 2.92 | 23 | 3.69 | 1.31 | 3.09 | 0.74 |
| T | 4.15 | 3.14 | 25 | 3.72 | 1.13 | 3.19 | 0.47 |
| U | 2.70 | 3.19 | 25 | 3.67 | 1.54 | 2.96 | 0.55 |
| V | 11.02 | 2.91 | 25 | 3.64 | 0.55 | 3.37 | 0.24 |
| X | 14.63 | 2.80 | 25 | 3.71 | 1.83 | 2.87 | 0.55 |

(1) Water content by Karl Fisher method (ASTM E203);
(2) ASTM D-664, utilising organic buffer (OB) as reference;
(3) Number of latent variables (LV).

The invention claimed is:

1. A method for determining a total acid number and naphthenic acid number of a sample selected from the group consisting of petroleum, petroleum cuts, and petroleum emulsions of water-in-oil type by mid-infrared attenuated total reflection Fourier transform infrared spectroscopy, the method comprising the following steps:

a) measuring absorbance, at a temperature between 21 and 28° C., and at a wave number selected within 1002-1351 $cm^{-1}$ and 1550-1822 $cm^{-1}$ of a plurality of samples to determine total acid number as determined by ASTM D-664 and napthenic acid number of a known amount of naphthenic acids;

b) obtaining at least one calibration curve, by multivariate regression model, correlating absorbance measured in step a) with values of total acid number and napthenic acid number of the plurality of samples at the wave number used in step a);

c) determining total acid number and napthenic acid number of additional samples by measuring absorbance using attenuated total reflection Fourier transform infrared spectroscopy at the temperature and wave number in step a) and using the calibration curves obtained in step b) to determine corresponding values.

2. The method according to claim 1 wherein a total attenuated reflectance accessory is equipped with a zinc selenide (ZnSe) crystal having approximately 12 reflections.

3. The method according to claim 1 wherein the multivariate regression model employed is preferentially the model based on partial least squares regression.

4. The method according to claim 1 wherein determinations to be realised on petroleum emulsions of water-in-oil type are restricted to samples containing up to 15% by weight of water.

* * * * *